US009332926B2

(12) United States Patent
Krieger et al.

(10) Patent No.: US 9,332,926 B2
(45) Date of Patent: May 10, 2016

(54) MRI IMAGING PROBE

(75) Inventors: Axel Krieger, Alexandria, VA (US);
Daniel Wayers, Oshkosh, WI (US);
Kenneth Bradshaw, Etobicoke (CA);
Stephen Abellera, Toronto (CA);
Christine Iris Elliott, Toronto (CA);
Cameron Piron, Toronto (CA); Chris Luglnbuhl, Toronto (CA); Alex Wang, Mississauga (CA)

(73) Assignee: Invivo Corporation, Andover, MA (US)

( * ) Notice: Subject to any disclaimer, the term of this patent is extended or adjusted under 35 U.S.C. 154(b) by 1109 days.

(21) Appl. No.: 13/304,583

(22) Filed: Nov. 25, 2011

(65) Prior Publication Data
US 2012/0242337 A1    Sep. 27, 2012

Related U.S. Application Data

(60) Provisional application No. 61/417,270, filed on Nov. 25, 2010, provisional application No. 61/417,271, filed on Nov. 25, 2010.

(51) Int. Cl.
*A61B 5/055*    (2006.01)
*A61B 5/00*    (2006.01)
*G01R 33/34*    (2006.01)
*G01R 33/28*    (2006.01)
(Continued)

(52) U.S. Cl.
CPC .............. *A61B 5/055* (2013.01); *A61B 5/6847* (2013.01); *G01R 33/287* (2013.01); *G01R 33/34084* (2013.01); *A61B 2017/00274* (2013.01); *A61B 2017/3411* (2013.01); *A61B 2017/3413* (2013.01); *A61B 2019/5236* (2013.01); *G01R 33/286* (2013.01)

(58) Field of Classification Search
CPC .............. G01R 1/06; G01R 1/07; A61B 5/055
See application file for complete search history.

(56) References Cited

U.S. PATENT DOCUMENTS 3,115,140 A    12/1963    Volkman
3,523,251 A *   8/1970    Halstead ...................... 455/282
(Continued)

FOREIGN PATENT DOCUMENTS

CN    1640139 A    7/2005
CN    101601266 A   12/2009
(Continued)

OTHER PUBLICATIONS

Lanz et al., "A High-Throughput Eight-Channel Probe Head for Murine MRI at 9.4 T", Magnetnic Resonance in Medicine 64:80-87, 2010.*
International Search Report for International Application No. PCT/CA2010/001228 mailed Oct. 2, 2011, 5 pages.
European Search Report mailed Mar. 1, 2012 for European Patent Application No. 07800538.6, 8 pages.
European Search Report for European Patent Application No. 07800538.6 mailed Mar. 1, 2012, 8 pages.
Piron, Cameron A., Hybrid Imaging Guidance System for Biopsy of the Breast, Thesis Paper, University of Toronto, 2001.
(Continued)

*Primary Examiner* — Tse Chen
*Assistant Examiner* — Joanne Hoffman

(57) ABSTRACT

A magnetic resonance imaging (MRI) probe includes a coil section having an imaging coil, and a handle section connected to the coil section. The handle section has a phase shifter circuit with inductors, capacitors, and coax line electrically connected and is configured to provide appropriate phase shift. The handle section further has a coaxial cable winding electrically connected to the imaging coil, and wound cylindrically, and has a slot therethrough between the ends of the cylindrical winding. The handle section further has a pre-amp circuit mounted on a substrate and electrically connected to the cylindrical coax winding.

20 Claims, 11 Drawing Sheets

(51) Int. Cl.
*A61B 17/00* (2006.01)
*A61B 17/34* (2006.01)
*A61B 19/00* (2006.01)

(56) References Cited

U.S. PATENT DOCUMENTS

| | | | |
|---|---|---|---|
| 4,503,844 A | 3/1985 | Siczek | |
| 4,552,346 A | 11/1985 | Schnelle et al. | |
| 4,572,203 A | 2/1986 | Feinstein | |
| 4,733,661 A | 3/1988 | Palestrant | |
| 4,825,162 A | 4/1989 | Roemer et al. | |
| 4,930,516 A | 6/1990 | Alfano et al. | |
| 4,930,525 A | 6/1990 | Palestrant | |
| 4,943,986 A | 7/1990 | Barbarisi | |
| 4,989,608 A | 2/1991 | Ratner | |
| 5,014,968 A | 5/1991 | Lammers et al. | |
| 5,047,036 A | 9/1991 | Koutrouvelis | |
| 5,072,721 A | 12/1991 | Weiler et al. | |
| 5,096,216 A | 3/1992 | McCalla | |
| 5,154,179 A | 10/1992 | Ratner | |
| 5,158,088 A * | 10/1992 | Nelson | A61B 8/0833 600/461 |
| 5,196,019 A | 3/1993 | Davis et al. | |
| 5,297,551 A | 3/1994 | Margosian et al. | |
| 5,308,352 A | 5/1994 | Koutrouvelis | |
| 5,426,685 A | 6/1995 | Pellegrino et al. | |
| 5,534,869 A * | 7/1996 | Harman | 342/27 |
| 5,548,218 A | 8/1996 | Lu | |
| 5,569,266 A | 10/1996 | Siczek | |
| 5,575,798 A | 11/1996 | Koutrouvelis | |
| 5,590,653 A | 1/1997 | Aida et al. | |
| 5,590,655 A | 1/1997 | Hussman | |
| 5,594,337 A | 1/1997 | Boskamp | |
| 5,678,549 A | 10/1997 | Heywang-Koebrunner et al. | |
| 5,682,098 A | 10/1997 | Vij | |
| 5,682,890 A | 11/1997 | Kormos et al. | |
| 5,706,812 A | 1/1998 | Strenk et al. | |
| 5,744,958 A | 4/1998 | Werne | |
| 5,782,764 A | 7/1998 | Werne | |
| 5,817,023 A | 10/1998 | William Daft | |
| 5,855,554 A | 1/1999 | Schneider et al. | |
| 5,868,673 A | 2/1999 | Vesely | |
| 5,868,757 A | 2/1999 | Koutrouvelis | |
| 5,944,023 A | 8/1999 | Johnson et al. | |
| 6,051,974 A | 4/2000 | Reisker | |
| 6,066,102 A | 5/2000 | Townsend et al. | |
| 6,091,985 A | 7/2000 | Alfano et al. | |
| 6,159,221 A | 12/2000 | Chakeres | |
| 6,163,616 A | 12/2000 | Feldman | |
| 6,163,717 A | 12/2000 | Su | |
| 6,174,291 B1 | 1/2001 | McMahon et al. | |
| 6,201,392 B1 | 3/2001 | Anderson et al. | |
| 6,229,145 B1 | 5/2001 | Weinberg | |
| 6,263,229 B1 * | 7/2001 | Atalar et al. | 600/423 |
| 6,281,681 B1 | 8/2001 | Cline et al. | |
| 6,295,671 B1 | 10/2001 | Reesby et al. | |
| 6,298,506 B1 | 10/2001 | Heinold et al. | |
| 6,302,579 B1 | 10/2001 | Meyer et al. | |
| 6,324,243 B1 | 11/2001 | Edic et al. | |
| 6,334,067 B1 | 12/2001 | Brabrand | |
| 6,421,454 B1 | 7/2002 | Burke et al. | |
| 6,421,553 B1 | 7/2002 | Costa et al. | |
| 6,437,567 B1 | 8/2002 | Schenck et al. | |
| 6,446,286 B1 | 9/2002 | Karmalawy | |
| 6,459,923 B1 | 10/2002 | Plewes et al. | |
| 6,470,204 B1 * | 10/2002 | Uzgiris | A61B 5/055 600/411 |
| 6,498,489 B1 | 12/2002 | Vij | |
| 6,501,980 B1 | 12/2002 | Carlon | |
| 6,521,209 B1 | 2/2003 | Meade et al. | |
| 6,526,299 B2 | 2/2003 | Pickard | |
| 6,591,128 B1 | 7/2003 | Wu et al. | |
| 6,593,101 B2 | 7/2003 | Richards-Kortum et al. | |
| 6,628,983 B1 | 9/2003 | Gagnon | |
| 6,639,406 B1 | 10/2003 | Boskamp et al. | |
| 6,640,364 B1 | 11/2003 | Josephson et al. | |
| 6,675,037 B1 | 1/2004 | Tsekos | |
| 6,697,652 B2 | 2/2004 | Georgakoudi et al. | |
| 6,723,303 B1 | 4/2004 | Quay | |
| 6,806,711 B2 | 10/2004 | Reykowski | |
| 6,810,595 B2 | 11/2004 | Chan | |
| 6,822,450 B2 | 11/2004 | Klinge et al. | |
| 6,867,593 B2 | 3/2005 | Menon et al. | |
| 6,904,305 B2 | 6/2005 | Tsekos | |
| 6,922,859 B2 | 8/2005 | Gagnon et al. | |
| 6,927,406 B2 | 8/2005 | Zyromski | |
| 6,950,492 B2 | 9/2005 | Besson | |
| 7,011,447 B2 | 3/2006 | Moyers | |
| 7,020,314 B1 | 3/2006 | Suri et al. | |
| 7,023,209 B2 | 4/2006 | Zhang et al. | |
| 7,024,027 B1 | 4/2006 | Suri et al. | |
| 7,024,711 B1 | 4/2006 | Stasney et al. | |
| D533,278 S | 12/2006 | Luginbuhl et al. | |
| 7,155,043 B2 | 12/2006 | Daw | |
| 7,166,113 B2 | 1/2007 | Arambula et al. | |
| 7,176,683 B2 | 2/2007 | Reeder et al. | |
| 7,245,125 B2 | 7/2007 | Harer et al. | |
| 7,245,694 B2 | 7/2007 | Jing et al. | |
| D569,977 S | 5/2008 | Luginbuhl et al. | |
| 7,373,676 B2 | 5/2008 | Markovic et al. | |
| 7,379,769 B2 | 5/2008 | Piron et al. | |
| 7,545,966 B2 | 6/2009 | Lewin et al. | |
| 7,583,786 B2 | 9/2009 | Jing et al. | |
| 7,656,993 B2 | 2/2010 | Hoernig | |
| 7,711,407 B2 | 5/2010 | Hughes et al. | |
| 7,809,426 B2 | 10/2010 | Kim et al. | |
| 7,881,428 B2 | 2/2011 | Jing et al. | |
| 7,908,690 B2 | 3/2011 | Luginbuhl et al. | |
| 7,925,328 B2 | 4/2011 | Urquhart et al. | |
| 7,937,132 B2 | 5/2011 | Piron et al. | |
| 7,970,452 B2 | 6/2011 | Piron et al. | |
| 8,050,736 B2 | 11/2011 | Piron et al. | |
| 8,155,417 B2 | 4/2012 | Piron et al. | |
| 8,162,847 B2 | 4/2012 | Wale et al. | |
| 8,162,848 B2 | 4/2012 | Hibner et al. | |
| 8,162,849 B2 | 4/2012 | Deshmukh et al. | |
| 8,241,301 B2 | 8/2012 | Zhang et al. | |
| 8,290,569 B2 | 10/2012 | Piron et al. | |
| 8,292,824 B2 | 10/2012 | Okada | |
| 8,298,245 B2 | 10/2012 | Li et al. | |
| 2001/0011394 A1 | 8/2001 | Heimbrock et al. | |
| 2001/0039378 A1 | 11/2001 | Lampman et al. | |
| 2002/0035864 A1 | 3/2002 | Paltieli et al. | |
| 2002/0056161 A1 | 5/2002 | Falbo et al. | |
| 2002/0073717 A1 | 6/2002 | Dean et al. | |
| 2002/0095730 A1 | 7/2002 | Al-Kassim et al. | |
| 2002/0099264 A1 | 7/2002 | Fontenot | |
| 2002/0131551 A1 | 9/2002 | Johnson et al. | |
| 2002/0156365 A1 | 10/2002 | Tsekos | |
| 2002/0156370 A1 | 10/2002 | Desouza | |
| 2002/0164810 A1 | 11/2002 | Dukor et al. | |
| 2002/0180442 A1 | 12/2002 | Vij | |
| 2002/0193815 A1 | 12/2002 | Foerster et al. | |
| 2003/0007598 A1 | 1/2003 | Wang et al. | |
| 2003/0191397 A1 | 10/2003 | Webb | |
| 2003/0194050 A1 | 10/2003 | Eberhard et al. | |
| 2003/0199753 A1 | 10/2003 | Hibner et al. | |
| 2003/0199754 A1 | 10/2003 | Hibner et al. | |
| 2003/0206019 A1 | 11/2003 | Boskamp | |
| 2004/0077972 A1 | 4/2004 | Tsonton et al. | |
| 2004/0081273 A1 | 4/2004 | Ning | |
| 2004/0183534 A1 | 9/2004 | Chan et al. | |
| 2004/0216233 A1 | 11/2004 | Ludwig et al. | |
| 2004/0220467 A1 | 11/2004 | Bonutti | |
| 2005/0005356 A1 | 1/2005 | Zacharopoulos et al. | |
| 2005/0033315 A1 | 2/2005 | Hankins | |
| 2005/0059877 A1 | 3/2005 | Falbo | |
| 2005/0080333 A1 | 4/2005 | Piron et al. | |
| 2005/0104591 A1 | 5/2005 | Qu et al. | |
| 2005/0228267 A1 | 10/2005 | Bulkes et al. | |
| 2005/0267373 A1 | 12/2005 | Lee | |
| 2006/0024132 A1 | 2/2006 | Seman | |
| 2006/0026761 A1 | 2/2006 | Falbo | |
| 2006/0106303 A1 * | 5/2006 | Karmarkar et al. | 600/422 |

(56) References Cited

U.S. PATENT DOCUMENTS

| | | | |
|---|---|---|---|
| 2006/0122630 A1 | 6/2006 | Daum et al. | |
| 2006/0133580 A1 | 6/2006 | Vezina | |
| 2006/0221942 A1 | 10/2006 | Fruth et al. | |
| 2006/0241408 A1 | 10/2006 | Yakubovsky et al. | |
| 2007/0016003 A1 | 1/2007 | Piron et al. | |
| 2007/0038144 A1 | 2/2007 | Hughes et al. | |
| 2007/0039101 A1 | 2/2007 | Luginbuhl et al. | |
| 2007/0050908 A1 | 3/2007 | Kogan et al. | |
| 2007/0092059 A1 | 4/2007 | Wayne Eberhard et al. | |
| 2007/0149878 A1 | 6/2007 | Hankins | |
| 2007/0161935 A1 | 7/2007 | Torrie et al. | |
| 2007/0167725 A1* | 7/2007 | Tropp et al. | 600/410 |
| 2007/0167769 A1 | 7/2007 | Ikuma et al. | |
| 2007/0233157 A1 | 10/2007 | Mark et al. | |
| 2007/0238949 A1 | 10/2007 | Wang et al. | |
| 2007/0255168 A1 | 11/2007 | Hibner et al. | |
| 2007/0255170 A1 | 11/2007 | Hibner et al. | |
| 2007/0276234 A1 | 11/2007 | Shahidi | |
| 2008/0005838 A1 | 1/2008 | Wan Fong et al. | |
| 2008/0033454 A1 | 2/2008 | Lukoschek et al. | |
| 2008/0077005 A1 | 3/2008 | Piron et al. | |
| 2008/0095421 A1 | 4/2008 | Sun et al. | |
| 2008/0132785 A1 | 6/2008 | Piron et al. | |
| 2008/0132912 A1 | 6/2008 | Shabaz | |
| 2008/0216239 A1 | 9/2008 | Luginbuhl et al. | |
| 2008/0230074 A1 | 9/2008 | Zheng et al. | |
| 2008/0234569 A1 | 9/2008 | Tidhar et al. | |
| 2008/0255443 A1 | 10/2008 | Piron et al. | |
| 2008/0306377 A1 | 12/2008 | Piron et al. | |
| 2009/0149738 A1 | 6/2009 | Piron et al. | |
| 2009/0156961 A1 | 6/2009 | Tsonton et al. | |
| 2009/0216110 A1 | 8/2009 | Piron et al. | |
| 2009/0222229 A1 | 9/2009 | Kakinami | |
| 2009/0247861 A1 | 10/2009 | Manus et al. | |
| 2009/0270725 A1 | 10/2009 | Leimbach et al. | |
| 2009/0275830 A1 | 11/2009 | Falco et al. | |
| 2010/0041990 A1 | 2/2010 | Schlitt et al. | |
| 2010/0249595 A1 | 9/2010 | Xu et al. | |
| 2010/0280354 A1 | 11/2010 | Zhang et al. | |
| 2010/0324445 A1 | 12/2010 | Mollere et al. | |
| 2010/0324448 A1 | 12/2010 | Mollere | |
| 2011/0034796 A1 | 2/2011 | Ma et al. | |
| 2011/0134113 A1 | 6/2011 | Ma et al. | |
| 2011/0152714 A1 | 6/2011 | Luginbuhl et al. | |
| 2011/0153254 A1 | 6/2011 | Hartov et al. | |
| 2011/0173753 A1 | 7/2011 | Luginbuhl et al. | |
| 2012/0172704 A1 | 7/2012 | Piron et al. | |
| 2013/0053684 A1 | 2/2013 | Piron et al. | |
| 2013/0137969 A1 | 5/2013 | Jones | |

FOREIGN PATENT DOCUMENTS

| | | |
|---|---|---|
| EP | 0396866 A2 | 11/1990 |
| EP | 0753758 A1 | 1/1997 |
| EP | 2445413 A1 | 5/2012 |
| EP | 2503934 A1 | 10/2012 |
| WO | 9608199 A1 | 3/1996 |
| WO | 01/28412 A1 | 4/2001 |
| WO | 02/39135 A2 | 5/2002 |
| WO | 2006017172 A1 | 2/2006 |
| WO | 2007070285 A2 | 6/2007 |
| WO | 2008064271 A2 | 5/2008 |
| WO | 2010078048 A2 | 7/2010 |
| WO | 2010148503 A1 | 12/2010 |
| WO | 2011014966 A1 | 2/2011 |
| WO | 2011134113 A1 | 11/2011 |
| WO | 2013001377 A2 | 1/2013 |

OTHER PUBLICATIONS

Palmer, Gregory, et al., "Optimal Methods for Fluorescence and Diffuse Reflectance Measurements of Tissue Biopsy Samples," Lasers in Surgery and Medicine, 30:191-200 (2002).
Kline, Nicole, et al., "Raman Chemical Imaging of Breast Tissue," Journal of Raman Spectroscopy, vol. 28, 119-124 (1997).
Manoharan, Ramasamy, et al., "Histochemical Analysis of Biological Tissues Using Raman Spectroscopy," Spectrochimica Acta Part A.52 (1996) 215-249.
Shafer-Peltier, K.E. et al. "Raman Microspectroscopic Model of Human Breast Tissue: Implications for Breast Cancer Diagnosis in Vivo" Journal of Raman Spectroscopy V.33 (2002).
Ntziachristos V., et al. "Concurrent MRI and Diffuse Optical Tomography of Breast After Indocyanine Green Enhancement," PNAS, Mar. 14, 2000, vol. 97, No. 6, 2767-2772.
Buadu LD, et al., Breast Lesions: Correlation of Contrast Medium Enhancement Patterns on MR Images with Histopathologic Findings and Tumor Angiogenesis.
Kriege, M., et al., "Efficacy of MRI and Mammography for Breast-Cancer Screening in Women with Familial or Genetic Predisposition," N Engl J Med 351:427-437 (2004).
Non-Final Office Action mailed Feb. 9, 2007 in U.S. Appl. No. 10/916,738.
Response to Feb. 9, 2007 Office Action in U.S. Appl. No. 10/916,738, Jul. 11, 2007.
Non-Final Office Action mailed Sep. 24, 2007 in U.S. Appl. No. 10/916,738.
Response to Sep. 24, 2007 Office Action in U.S. Appl. No. 10/916,738, Dec. 26, 2007.
Non-Final Office Action mailed Nov. 16, 2009 in U.S. Appl. No. 11/442,944.
Response to Nov. 16, 2009 Office Action in U.S. Appl. No. 11/442,944, May 17, 2010.
Non-Final Office Action mailed May 12, 2009 in U.S. Appl. No. 12/031,271.
Response to May 12, 2009 Office Action in U.S. Appl. No. 12/031,271, Nov. 12, 2009.
Final Office Action mailed Feb. 5, 2010 in U.S. Appl. No. 12/031,271.
Response to Feb. 5, 2010 Office Action in U.S. Appl. No. 12/031,271, Aug. 5, 2010.
Non-Final Office Action mailed Jan. 22, 2010 in U.S. Appl. No. 11/447,053.
Response to Jan. 22, 2010 Office Action in U.S. Appl. No. 11/447,053, Jul. 22, 2010.
International Search Report mailed Dec. 13, 2007 in International Application No. PCT/CA2007/001513.
International Preliminary Report on Patentability issued Mar. 3, 2009 in International Application No. PCT/CA2007/001513.
European Search Report mailed Jul. 30, 2009 in EP Application No. 09007010.3.
European Search Report mailed Oct. 16, 2009 in EP Application No. 09007010.3.
General Electric—Press Release—"GE Healthcare Introduces Ultrasound Fusion; New LOGIQ E9 Merges Real-time Ultrasound with CT, MR and PET," Sep. 2, 2008, 2 pages.
International Preliminary Report of Patentability for International Application No. PCT/CA2010/001871 dated May 30, 2012, 1 page.
International Search Report and Written Opinion of the International Searching Authority for International Application No. PCT/CA2010/001871 dated Mar. 8, 2011, 9 pages.
M. Berger, "Image Fusion and Needle Guidance in Ultrasound", General Electric, Power Point Presentation, date unknown, 17 pages.
P. Mullen and C. Owen, "MR, Ultrasound Fusion: Bridging the Gap Between Clinical Benefits, Access and Equipment Utilization," SignaPULSE—A GE Healthcare MR Publication, Spring 2009, 5 pages.
Update of AAPM Task Group No. 43 Report: A revised AAPM protocol for brachytherapy does calculations; Med. Phys. vol. 31 No. 3, Mar. 2004; pp. 633-674.
Supplement to the 2004 update of the AAPM Task Group No. 43 Report; Med. Phys. vol. 34 No. 6, Jun. 2007; pp. 2187-2206.
Erratum: "Update of AAPM Task Group No. 43 Report: A revised AAPM protocol for brachytherapy dose calculations" [Med. Phys. 31, 633-674 (2004)].
International Preliminary Report on Patentability for PCT/CA10/000973, dated Jan. 4, 2012.
International Search Report for International Application No. PCT/CA2010/000973, mailed Oct. 1, 2010, 3 pages.
Pagoulatos et al., "Interactive 3-D Registration of Ultrasound and Magnetic Resonance Images Based on a Magnetic Position Sensor," IEEE Transactions on Information Technology in Biomedicine, vol. 3, No. 4, Dec. 1999, 11 pages.

* cited by examiner

MRI IMAGING PROBE

RELATED APPLICATIONS

This application claims priority from U.S. Provisional Patent Application No. 61/417,270 filed Nov. 25, 2010 and U.S. Provisional Application No. 61/417,271 filed Nov. 25, 2010, the contents of each of which are herein incorporated by reference.

FIELD OF INVENTION

This invention relates to the field of medical imaging and more specifically to the field of magnetic resonance imaging (MRI).

SUMMARY OF THE INVENTION

In an aspect of the present invention, there is a MRI imaging probe comprising a coil section having an imaging coil and a handle section connected to the coil section. The handle section having a phase shifter circuit comprising a first set of inductors and capacitors electrically connected, a coaxial cable winding electrically connected to the imaging coil and wound cylindrically, and having a slot therethrough between the ends of the cylindrical winding. The handle section further having a pre-amp circuit mounted on a substrate and electrically connected to the cylindrical winding, wherein at least a portion of the substrate is contained within the slot of the coaxial cable winding.

The imaging coil may have a passive tuning circuit. The probe may further comprise a fiducial marker in the coil section. The coil section and the handle section may be substantially cylindrical. The MRI probe may further comprise a substantially cylindrical neck section connecting the coil section to the handle section. The neck section may have a smaller diameter than that of the coil and handle sections. The coil section, handle section and neck portion may be aligned along a longitudinal axis. The substrate may be substantially planar and may be parallel to the longitudinal axis. The slot may be aligned along the longitudinal axis.

The MRI imaging probe may further comprise a second imaging coil in the coil section. The second imaging coil may have a second passive tuning circuit, and may be electrically connected to the first imaging coil through a decoupling circuit. There may also be a second set of inductors and capacitors electrically connected, a second coaxial cable winding electrically connected to the second imaging coil and wound cylindrically around the slot of the first cylindrical winding. There may also be a second pre-amp circuit mounted on the substrate electrically connected to the second cylindrical winding.

The first and second coaxial cylindrical windings may be wound radially relative to each other. The first and second cylindrical windings may also be wound side-by-side. The decoupling circuit may comprise a decoupling capacitor.

The MRI imaging probe may further comprise a coil shell substantially surrounding the coil section and the neck section. The coil shell may comprises a slot therethrough, the slot permitting passage through the coil section of the probe. The coil section may also have a passage therethrough, the passage being aligned with the slot of the coil shell. The slot may extend from a first surface region of the coil shell at the neck section, to a second surface region of the coil shell at the coil section.

The coil shell may have a smaller diameter around the neck section than around the coil section. The MRI imaging probe may further comprise a handle shell substantially surrounding the handle section, and the handle shell may be connected to the coil shell.

BRIEF DESCRIPTION OF THE FIGURES

For a better understanding of embodiments of the system and methods described herein, and to show more clearly how they may be carried into effect, reference will be made by way of example, to the accompanying drawings in which.

DETAILED DESCRIPTION

Figure 1:
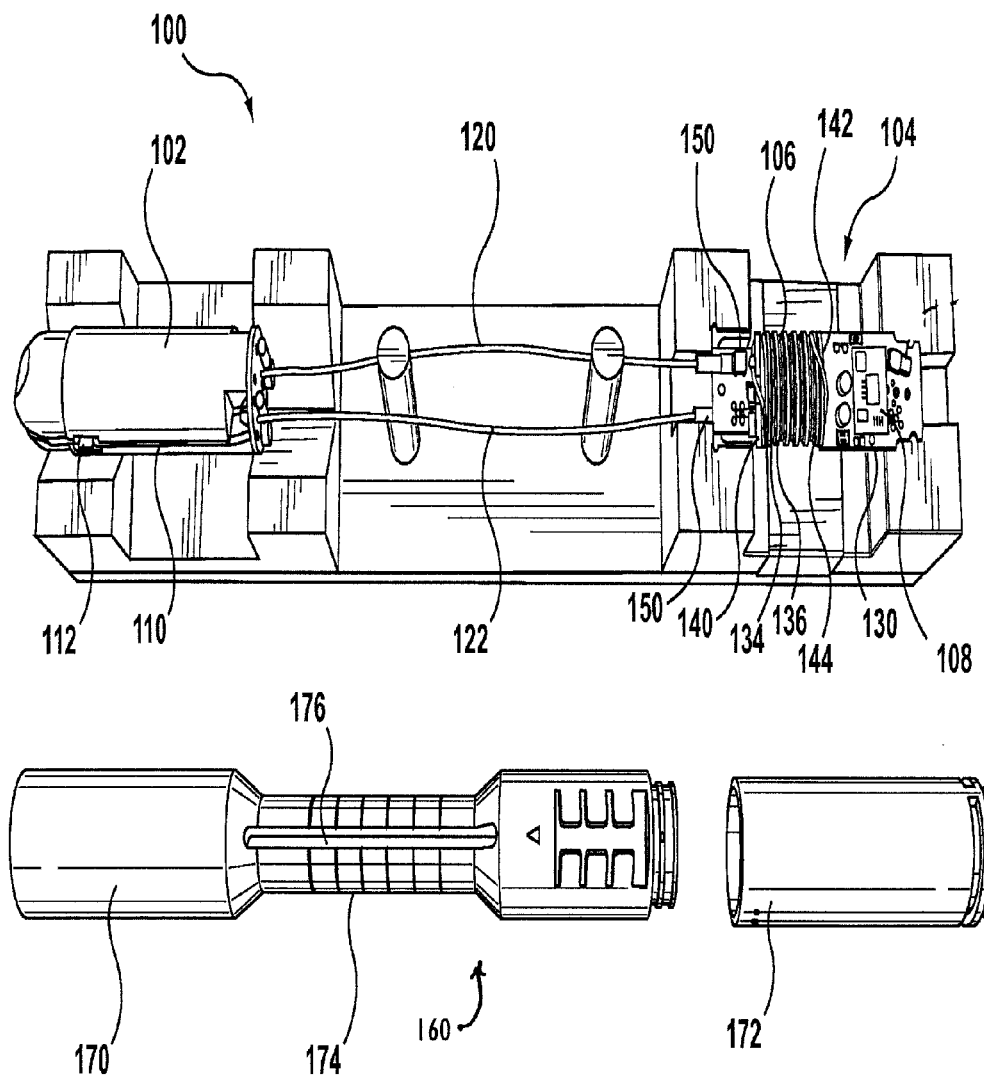
FIG. 1 shows an exploded view of an embodiment of an MRI imaging probe.

It will be appreciated that for simplicity and clarity of illustration, where considered appropriate, reference numerals may be repeated among the figures to indicate corresponding or analogous elements or steps. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Furthermore, this description is not to be considered as limiting the scope of the embodiments described herein in any way, but rather as merely describing the implementation of the various embodiments described herein.

Prostate diseases represent a significant health problem. In the United States, metastatic prostate cancer is currently the third leading cause of death among the American men over fifty years, resulting in approximately 31,000 deaths annually. The definitive diagnostic method of prostate cancer tends to be core needle biopsy. Currently, transrectal ultrasound (TRUS) guided needle biopsy is a technique being utilized for the diagnosis of prostate cancer and contemporary intraprostatic delivery of therapeutics tends to be also primarily performed under TRUS guidance. This technique has been popular due to its specificity, real-time nature, low cost, and apparent simplicity. At the same time, however, TRUS-guided biopsy also tends to fail to correctly detect the presence of prostate cancer in approximately 20% of cases.

Magnetic resonance imaging (MRI) detects faint nuclear magnetic resonance (NMR) signals given off by protons in the presence of a strong magnetic field after excitation by a radio frequency signal. The NMR signals are detected using antennae termed "coils". NMR signals are extremely faint, and so the ability for a coil to detect these signals tends to decrease with increasing distance between the coil and the tissue being imaged.

In typical operation, coils are be tuned to the Larmor frequency associated with the magnet field strength of the main MRI field (or $B_0$ field) in which it is meant to operate. For example, an MRI magnet having a 1.5 T main field requires a coil tuned to 63.86 MHz, and an MRI magnet having a main field of 3.0 T requires 127.7 MHz. In current commercial coils, the coil elements or antenna are typically inseparable from the patient support structure, or are inseparable from the coil housing.

Coils local to the tissue being imaged, such as the prostate, tend to have a higher signal-to-noise ratio (SNR) than coils positioned further away from the tissue, even if the coils that are positioned close to the tissue of interest are smaller than those positioned further away; however, due to the physical location of a person's prostate many existing MRI coils, such as surface coils, are ineffective at obtaining images of a prostate with a high SNR. However, if a coil can be inserted with a cavity of a patient such that it is closer in proximity to the prostate, or other tissue of interest, this can tend to be advantageous to improve SNR of the resulting MRI image obtained.

Additionally, in current MRI applications, due to the low currents and signals obtained by the coils due to the faint NMR signals, the signal obtained are boosted and/or filtered by a pre-amp circuit. However, in such MRI coil applications, the pre-amp circuits are not located proximate to the MRI coil, due to space constraints, especially for MRI coils intended for insertion inside an orifice of a patient, such as the rectum of a patient. To improve SNR of the resulting image it will tend to be advantageous to position the pre-amp circuit proximate the coils to avoid signal losses through lengthy transmission cables from the coil to the pre-amp circuit.

Another consideration for imaging is varying the position in which the tissue is imaged, for example being able to image a tissue in a patient when the patient is in multiple positions, such as the prone position (lying on their stomach), in the supine position (lying on their back) or when lying on their side.

Therefore, it may be desirable to have an improved MRI coil that having improved SNR capabilities that is portable and is capable of use within a cavity of a patient to image tissue that is otherwise difficult to obtain through traditional external MRI coils.

Referring to FIG. 1, MRI imaging probe 100 is shown in an exploded view. In the embodiment shown, MRI imaging probe has coil section 102 and handle section 104, with coil section 102 having imaging coil 110 and handle section 104 having phase shifting circuit 106 and pre-amp circuit 108.

In the embodiment shown, MRI imaging probe 100 is a two channel MRI imaging probe, having two MRI coils; however, in FIG. 1, only one of the two coils, coil 110, is visible with the other coil being hidden from view. In the embodiment shown in FIG. 1, coil 110 has passive tuning circuit 112 which operates as an impedance choke, and blocks out high induced currents, when activated by a PIN diode switched on by voltages induced by the RF transmit field of the MRI magnet when in use.

As discussed above, while not shown in FIG. 1, MRI imaging probe has two channels, having imaging coil 110 and a second imaging coil that is not visible. The two imaging coils are decoupled physically with a small overlap and through a decoupling capacitor (as discussed further below), configured to decouple the two coils and reduce signals in one coil that are induced from current, such as noise current, flowing in the other coil, which can tend to improve the SNR of MRI imaging probe 100.

Figure 3:
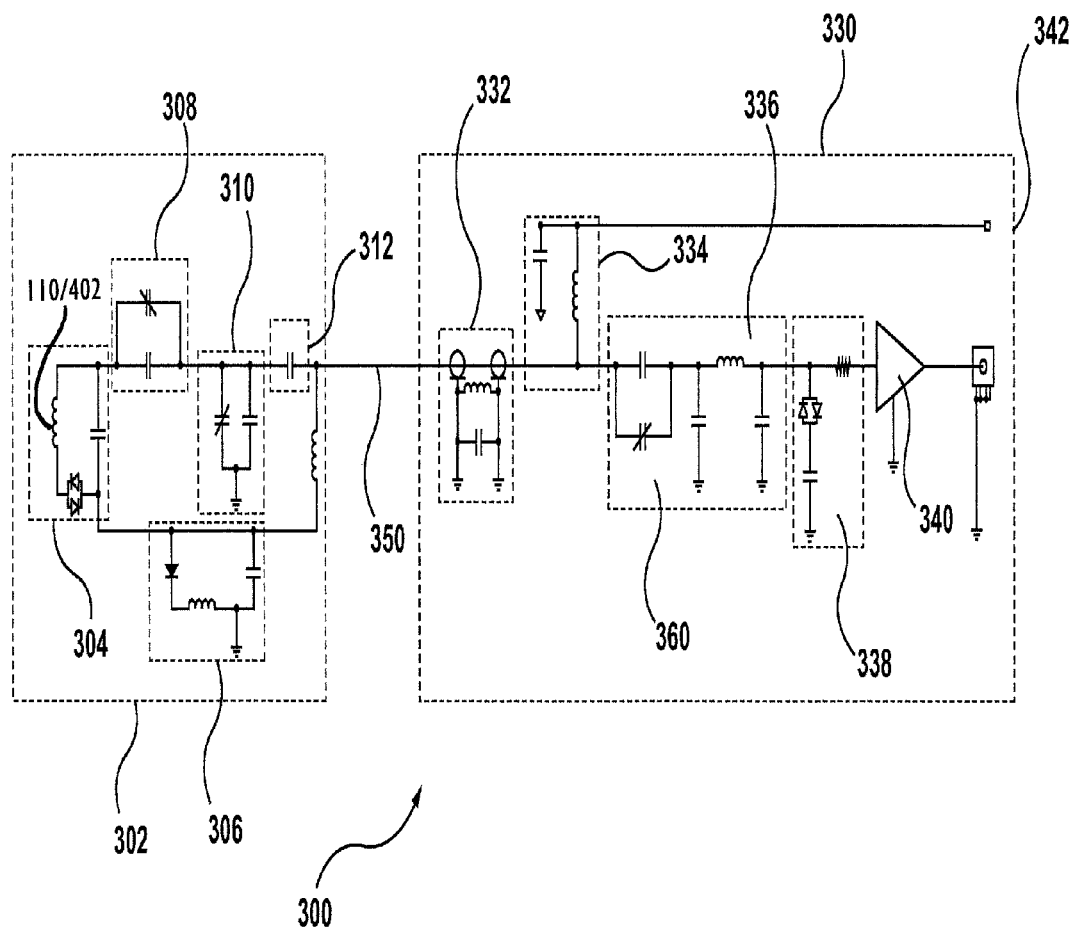
FIG. 3 shows a circuit diagram of an alternative embodiment of an MRI imaging probe.
Figure 4:
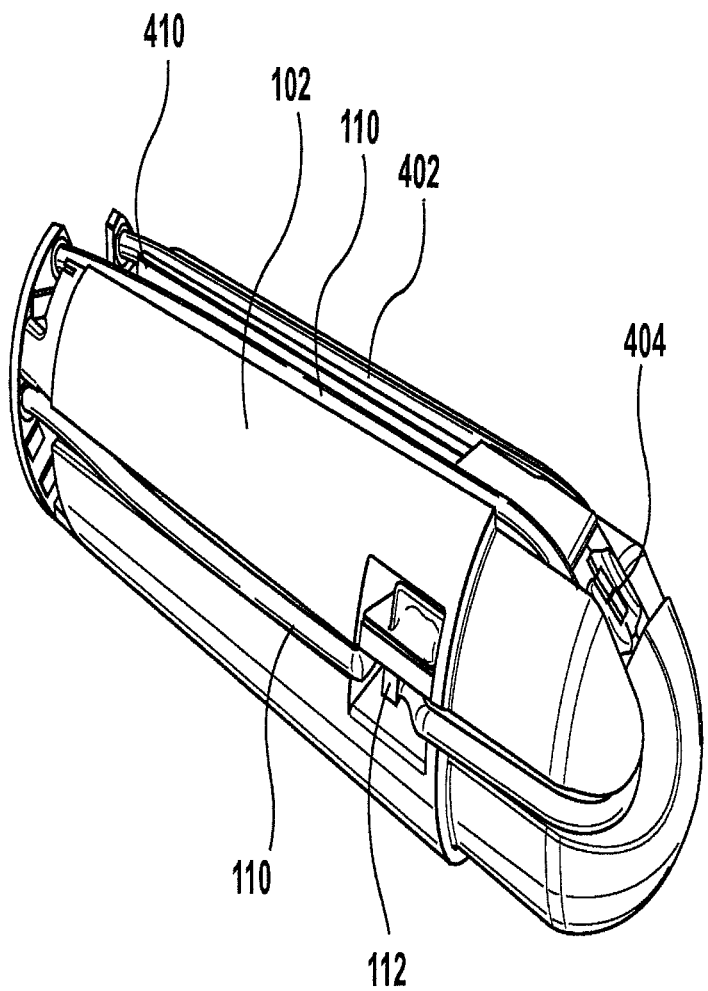
FIG. 4 shows an embodiment of a two channel MRI coil of an MRI imaging probe.
Figure 5:
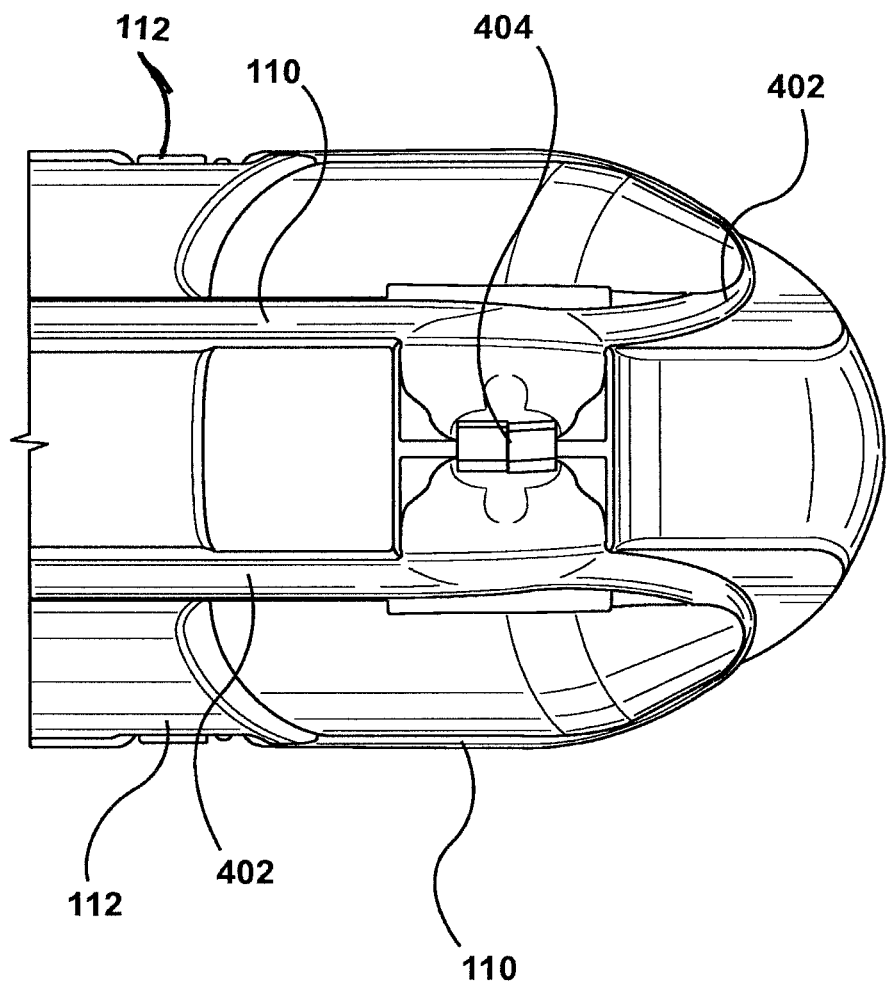
FIG. 5 shows an alternate view of the MRI coil shown in FIG. 4.

With reference to FIGS. 4 and 5 alternative views of coil section 102 is shown, where the two imaging coils 110 and 402 are shown. As shown in FIG. 4, coil 110 has passive tuning circuit 112 and while not visible, coil 402 has a corresponding passive tuning circuit positioned in a similar position in the other side of section 102 (See FIGS. 2 and 3)

Additionally, as shown in FIG. 4, coil section 102 contains passage 410, which can be used to position or allow a medical instrument or instruments to pass through, such as a biopsy needle, to allow a user to take biopsy samples from a tissue of interest in a patient through an orifice that coil section 102 is positioned within. For example, when coil section 102 of MRI imaging probe 100 is positioned within a patient's rectum through their anus, a user can position a biopsy needle through passage 410 to obtain biopsy tissue samples of a patient's prostate.

Referring to FIGS. 4 and 5, coils 110 and 402 decoupled physically with a small physical overlap and connected with a decoupling capacitor 404 which, as discussed above, is configured to decouple the two coils and reduce signals in one coil that are induced from current, such as noise current, flowing in the other coil, which can tend to decrease the SNR of MRI imaging probe 100.

Reference will now be made to various positions on coil section 102 that are visible in the Figures (such as the top, bottom and side relative to the view of the elements shown in the Figures); however, skilled persons will appreciate that the coil is not limited by the specific positional references made, and that the positional references are only referred to for the purpose of describing the elements in the Figures.

As shown in FIG. 4, coil 110 is position on the top of coil section 102 close to and along one side (referred to as the back side for convenience) of passage 410 while coil 402 is positioned close to and along the path of the other side (referred to as the front side for convenience) of passage 410. Decoupling capacitor 404 is positioned close to the tip of coil section 102 which, in the embodiment shown is a curved tip that can tend to provide improved patient comfort when inserted into an orifice of the patient.

Coil 110 and coil 402 are each decoupled physically with a small overlap of the coils and decoupled electrically by decoupling capacitor 404, with coil 110 continuing through decoupling capacitor 404 along the front side of coil section 102 and coil 402 continuing through decoupling capacitor 404 along the back side of coil section 102 (not visible in FIG. 4).

Figure 6:
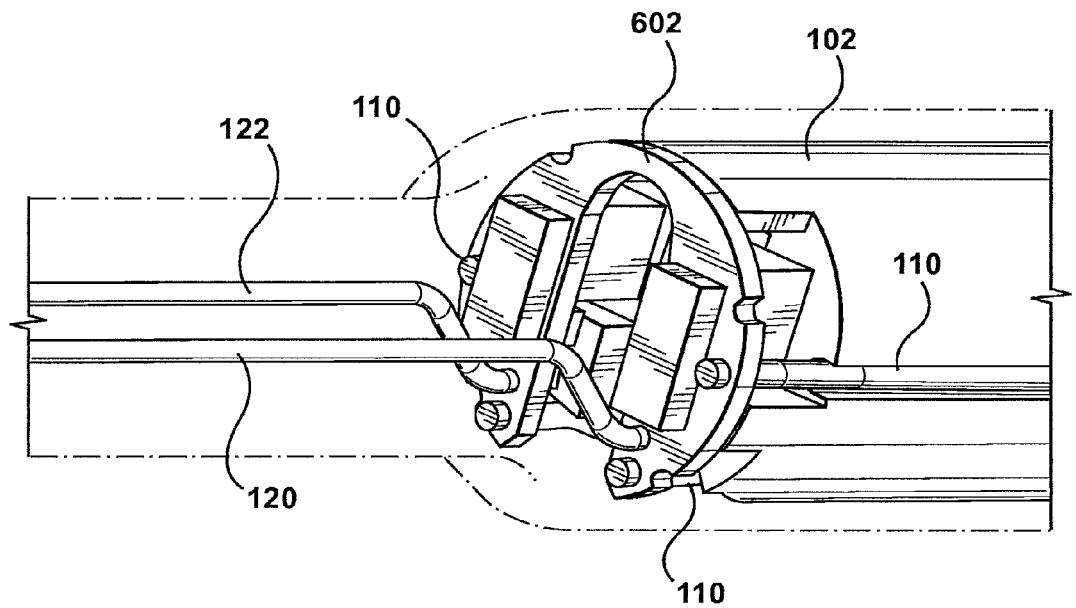
FIG. 6 shows an embodiment of the connection of the MRI coil shown in FIG. 4 with transmission cables.
Figure 7:
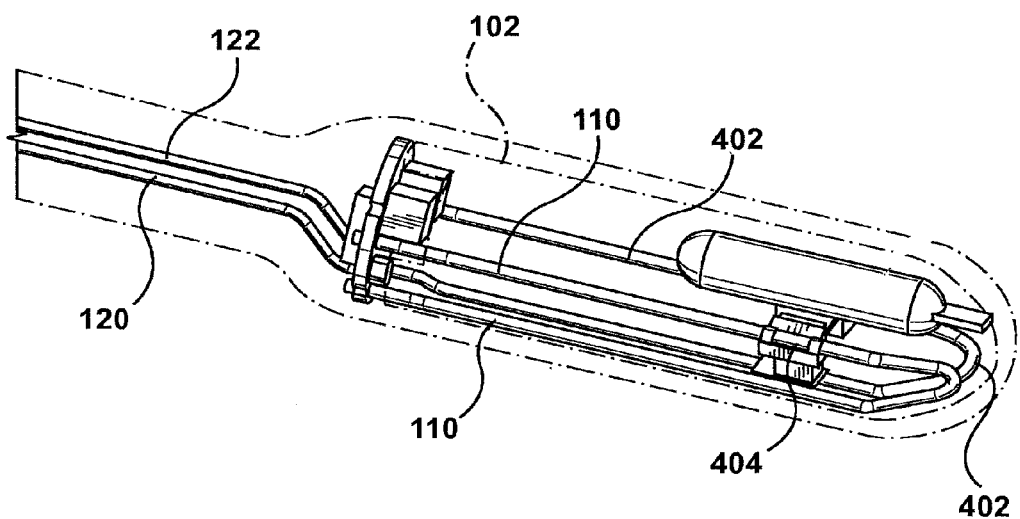
FIG. 7 shows an alternative embodiment of a MRI coil having a fiducial marker.

With reference to FIG. 6, coil 110 is electrically connected to transmission line 120 through backplate 602 and coil 402 is electrically connected to transmission line 122 through backplate 602; however, skilled persons will appreciate that in some embodiments, backplate 602 may not be used and transmission lines 120 and 122 may be electrically connected or coupled directly to coil 110 and 402 respectively.

Figure 9A:
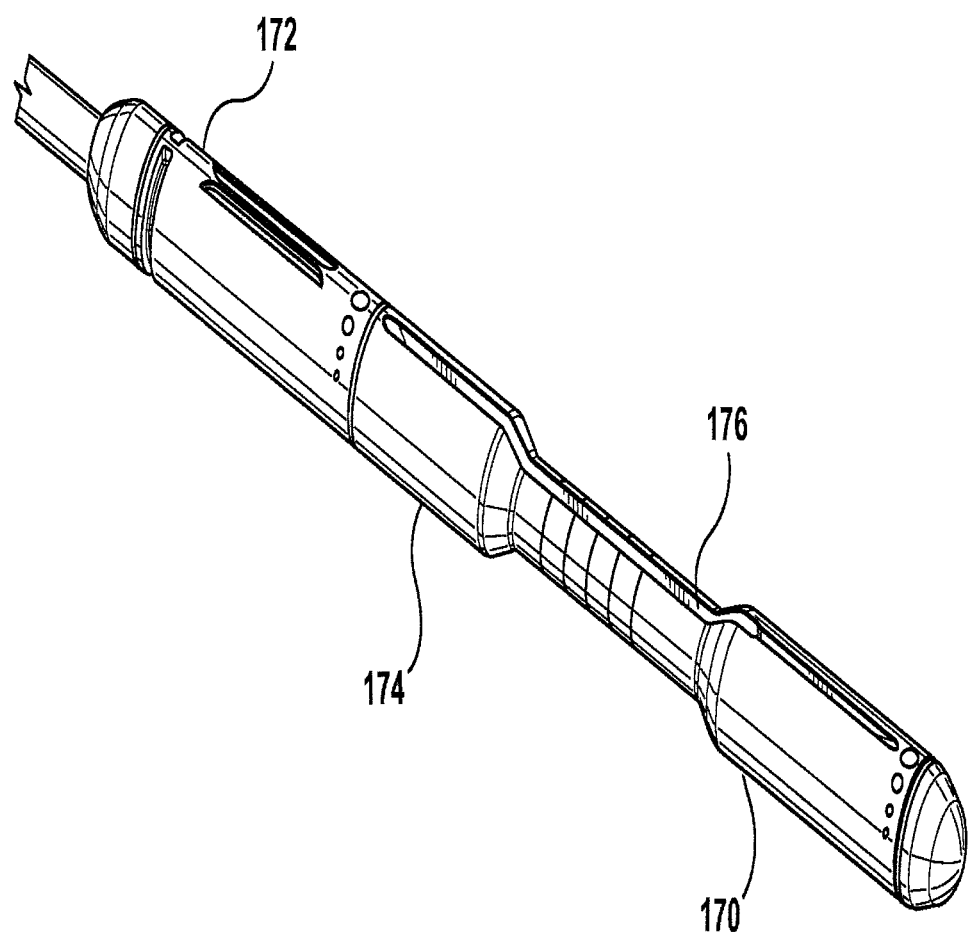
FIG. 9A to 9D shows an embodiment of an MRI imaging probe in a protective casing.
Figure 9B:
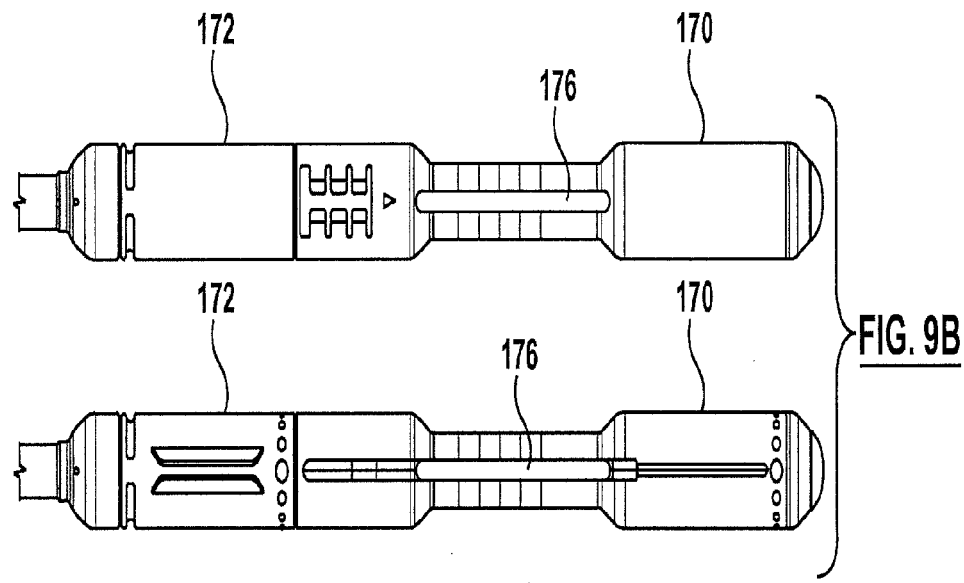
Figure 9C:
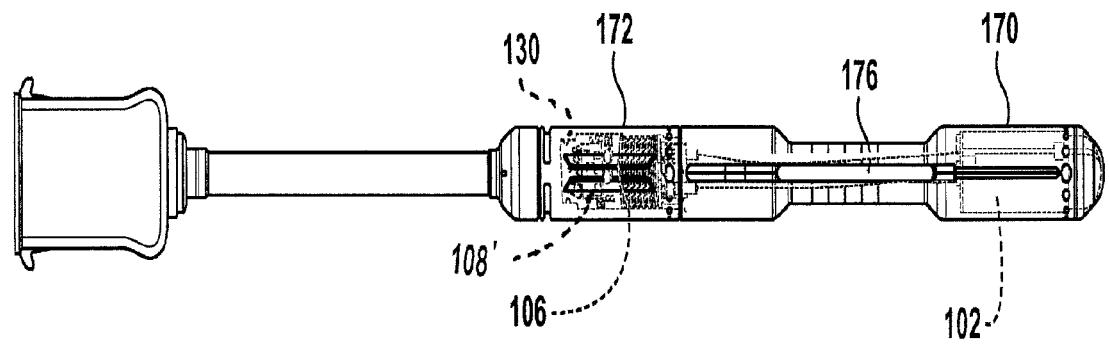
Figure 9D:
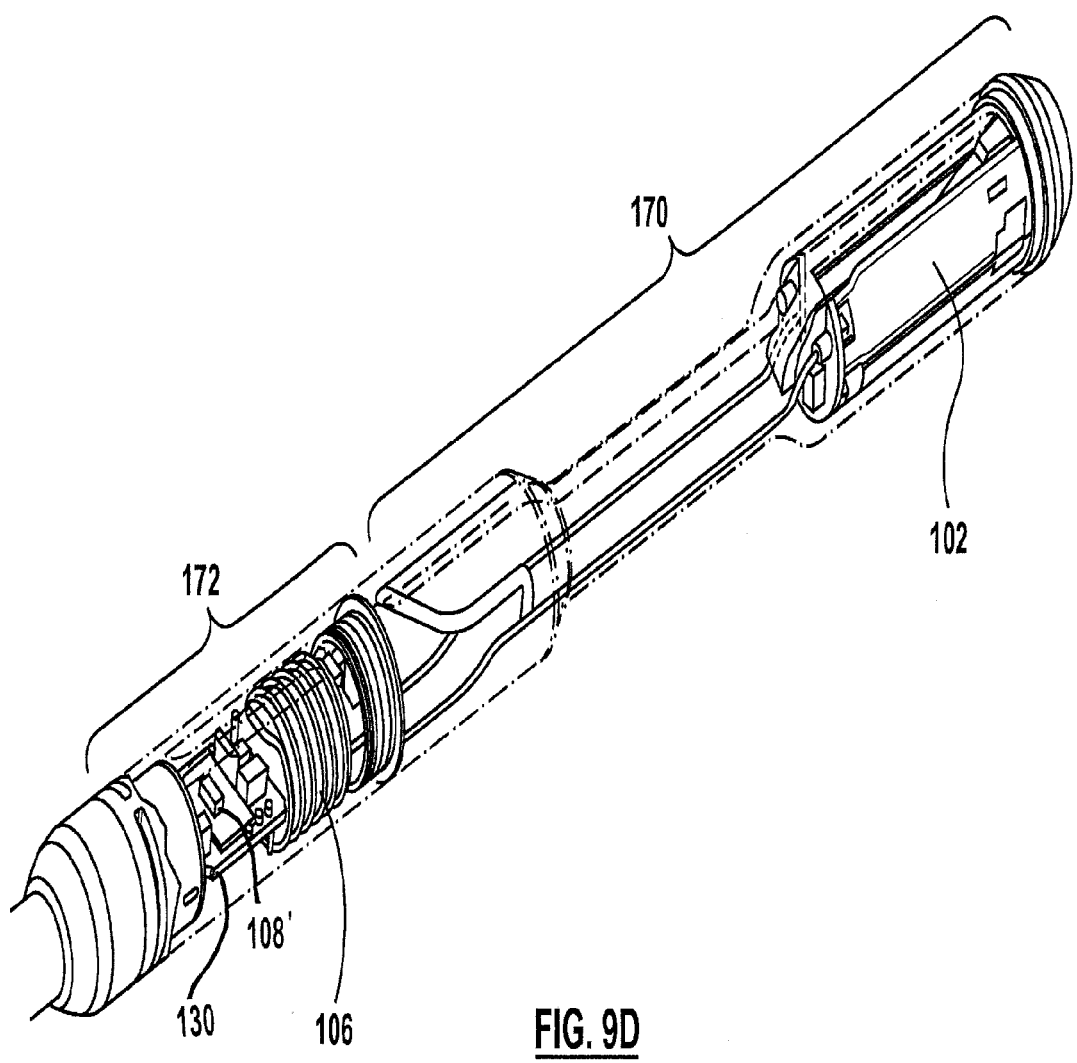

Referring back to FIG. 1, in the embodiment shown, handle portion 104 has substrate 130 on which pre-amp circuit 108 is mounted, and handle portion 104 additionally includes shifting circuit 106. In the embodiment shown, a second pre-amp circuit (not shown) is mounted on the reverse side (or underside, as shown) of substrate 130, each pre-amp circuit being associated with one of the two channels of MRI imaging probe 100; however, in other embodiments the second pre-amp circuit can be mounted on substrate 130 in another position. In the embodiment shown, pre-amp circuit 108 (as well as the second pre-amp circuit 108' in FIG. 9D) is a low input impedance device that has additional circuitry, to provide pre-amp decoupling which can tend to reduce current in coil 110 or 402 and reduce the coupling between coils 110 and 402.

Figure 8:
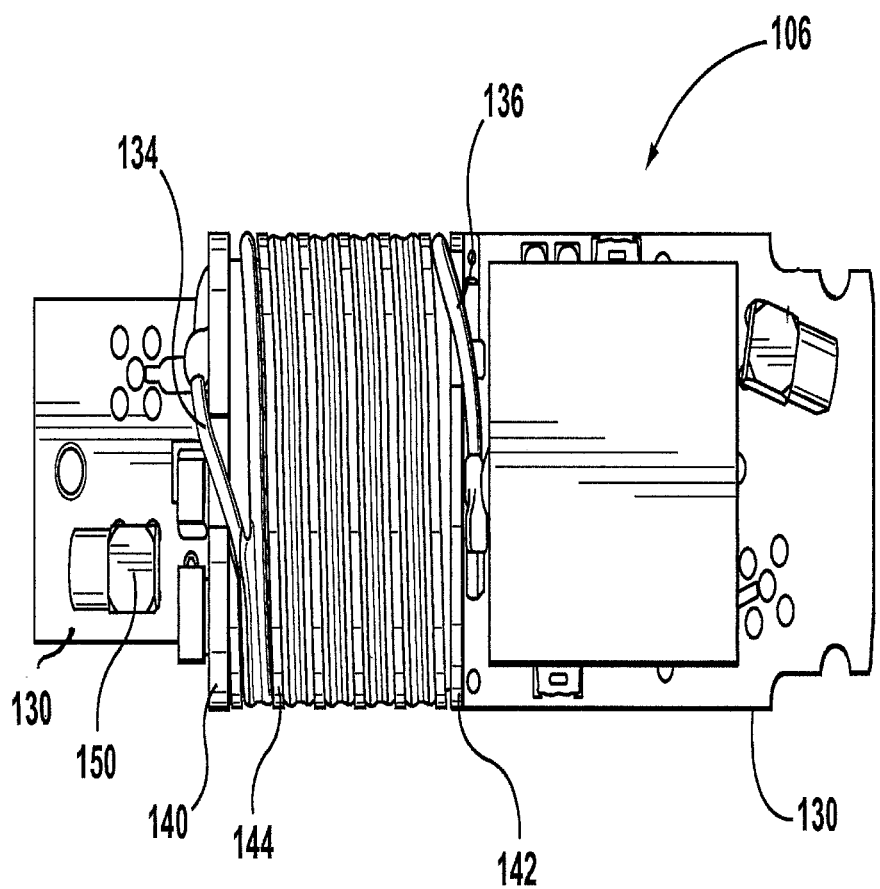
FIG. 8 shows an embodiment of a phase shifting and pre-amp circuit for use with an MRI imaging probe.

With additional reference to FIG. 8, phase shifting circuit 106 shifts the phase of the received input signal so that the input to pre-amp circuit 108 has the desired inductance such that it resonates with the capacitance in line with coil 110. This can tend to decouple the pre-amp from the coil to increase SNR and filter any unwanted noise generated by currents, such as noise currents, or other undesired signals. In the embodiment shown, phase shifting circuit 106 consists of an inductor and a capacitor for each input signal received (in the embodiment shown, being two input signals, one for each channel of MRI imaging probe 100) maintains the characteristic 50 ohms impedance which is necessary to proper noise matching for the preamp in the embodiment. It will be appreciated that in other embodiments, alternate circuits may be provided to shift the phase.

In the embodiment shown, phase shifting circuit 106 consists of two coaxial cables 134 and 136 wound cylindrically around cylinder 144 having groves therein to seat coaxial cables 134 and 136 in their desired position, and cylinder 144 further has end-caps 140 and 142, that are comprised of a substrate whereby further electrical components can be applied (in the embodiment shown, the capacitors of phase shifting circuit 106 are mounted on end-caps 140 and 142). In this embodiment, coaxial cables 134 and 136 form an inductance with their coax shields that can be resonated with appropriate capacitance to provide high impedance to surface currents on the coax shield. Additionally, in such embodiments, coaxial cables 134 and 136 can convert the signal generated by coils 110 and 402 from a balanced signal or output to an unbalanced signal or output.

In alternative embodiments, coaxial cables 134 and 136 can be wound cylindrically such as around substrate 104, but may not be mounted or positioned around any additional components (such as cylinder 144). In such embodiments, the stiffness of coaxial cables 134 and 136 may be such that they will not deform under normal operation.

In the embodiment shown in FIG. 8, coaxial cables 134 and 136 are wound side-by-side and held together by solder applied in between them; however, in alternative embodiments, coaxial cables 134 and 136 can be mounted radially, with one coaxial cable being mounted on top of the other in the cylindrical winding. In such alternative embodiments, coaxial cables 134 and 136 may be further soldered together.

In the embodiment shown, end-caps 140 and 142 have slots substantially centered in them and a portion of substrate 130 is inserted into end-caps 140 and 142 with a portion of substrate 130 projecting out of each slot. In such embodiments, the portion of substrate that is positioned between end-caps 140 and 142 can be serpentine shape, which can provide strain relief during thermal expansion.

In other embodiments, for example, in those embodiments having no end-caps 140 and 142, substrate 130 can be positioned in a slot, or cavity, formed within the cylindrical windings of coaxial cables 134 and 136 such that a portion of substrate 130 is positioned with the winding, and may project out of one or both sides of the windings.

Coil 110 is electrically connected to coaxial cable 134 by transmission line 120 and connector 150. In the embodiment shown, transmission line 120 is a coaxial cable and is connected to connector 150 through a threaded engagement; however, skilled persons will appreciate that the other means of electrically connecting transmission line 120 to coaxial cable 134 can be implemented.

Additionally, the second channel of MRI probe 100 comprising coil 402 that is not shown in FIG. 1, is connected to coaxial cable 136 through transmission line 122 and can be connected to coaxial cable 136 through a connector that is similar to connector 150 that, in the embodiment shown in FIG. 1 is positioned on the other side (or underside) of substrate 130 and is not shown.

In the embodiment shown, coaxial cable 134 is electrically connected to transmission line 120 at end-cap 140 and coaxial cable 136 is electrically connected to transmission line 122 at end cap 142. In this embodiment, when a first current (or signal) flows through coaxial cable 134 and a second current (or signal) flows through coaxial cable 136, each will be flowing in the opposite direction when MRI imaging probe 100 is in use.

Pre-amp circuit 108, in the embodiment shown, is electrically connected to signal output component 160 which can be electrically connected to a transmission cable or other signal line (not shown) for transmitting signals to an MRI workstation (not shown) for signal processing in order to generate an image of the tissue being imaged with MRI probe 100. In the embodiment shown, the second pre-amp circuit (not shown) that is positioned on the underside of substrate 130 has an additional signal output component (not shown) for transmitting signals generated by the second channel of MRI probe 100 for processing and generation of an MRI image of the tissue being imaged.

Referring again to FIG. 1, protective shell 160 is shown, having coil shell 170 and handle shell 172. MRI imaging probe 100 can be enclosed within protective shell 160 to protect the tissue of a patient that is being imaged by MRI imaging probe 100 from interfering with electrical components and to provide for the sterility of MRI probe 100. In the embodiment shown, coil shell component 170 is cylindrically shaped for a snug fit over coil section 102. In the embodiment shown, coil shell 170 further includes an integral neck shell 174 having a smaller diameter. In the embodiment shown, transmission lines 120 and 122 are positioned with neck shell 174 and extend out the end of coil shell 170. Skilled persons, however, will appreciate that neck shell 174 can be the same diameter as coil shell component 170, or may not be necessary for certain applications.

Figure 9E:
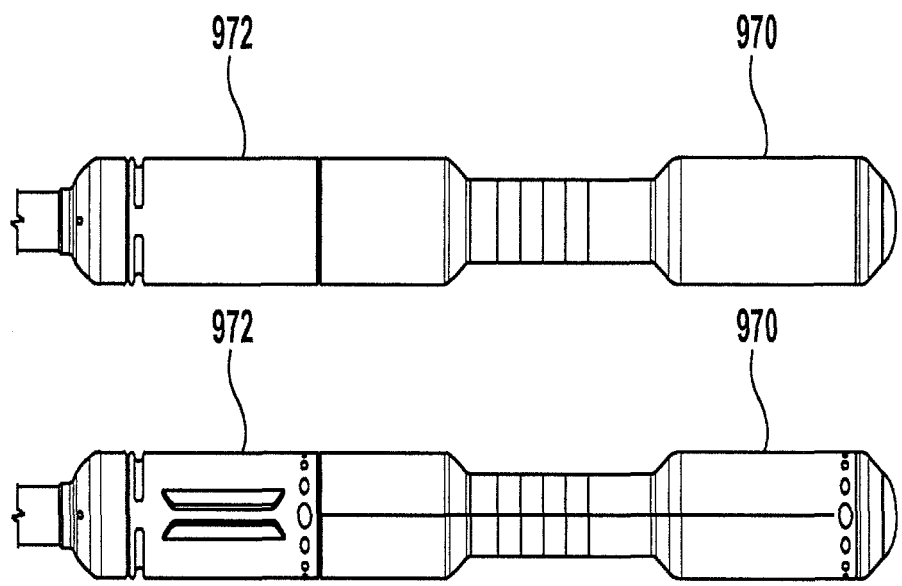
FIG. 9E shows an alternate embodiment of a protective casing.

Handle shell 172 fits over handle section 104 and covers substrate 130 and phase shifting circuit 106 to protect the electronics and to allow an operator to grip MRI imaging probe 100 when in use. In the embodiment shown, coil shell component 170 is removably connected to handle shell 172, and as shown coil shell component 170 has a fitment flange extending therefrom that is inserted into an end of handle shell 172 to form a frictional engagement; however, skill persons will appreciate that other means of attachment can be used, such as for example, a threaded connection. An embodiment of MRI imaging probe 100 contained in protective shell 160 is shown in FIG. 9A to 9D. In FIG. 9E, an alternate embodiment having a shell casing comprising coil shell 970 and handle shell 972 is shown.

In the embodiment shown, neck portion 174 includes slot 176 that can be used to position medical instruments therethrough, such as biopsy needles, so that when MRI imaging probe is in use, a biopsy needle can be inserted through the orifice that probe is inserted within to obtain a biopsy of a tissue being imaged by MRI imaging probe 100. In some embodiments, slot 176 can be aligned with passage 410 of coil section 102, shown on FIG. 4 and on other embodiments, slot 176 may not be necessary, for example in embodiments that are for imaging only or where alternative biopsy tools may be used.

In use, coil section 102 of the embodiment shown in FIG. 1, once encased in coil shell component 170, can be inserted through an orifice of a patient, such as the anus, and extended into the patient's rectum such that coil 110 is positioned close to the tissue near the patient's prostate or other tissue being imaged. In such uses, the anus may contract around neck portion 174 which can tend to offer additional patient comfort and to assist in preventing slippage of MRI imaging probe 100 when in use.

In such embodiments, at least a portion of neck portion 172 can be inserted past the anus and into the rectum of the patient such that slot 176 may have at least a portion of it (and in some embodiments, the aligned passage 410 of coil section 102) is within the rectum of the patient. When this is the case, medical instruments, such as a biopsy needle, can be inserted through the portion of slot 176 that is outside of the patient and can be positioned along the slot such that they pass through the slot beyond the patient's anus and into the rectum, where such medical instruments can be then manipulated so that the end of such instruments are delivered to the tissue of interest to, in some embodiments, obtain a biopsy sample (such as from the patient's prostate) for later analysis.

Figure 2:
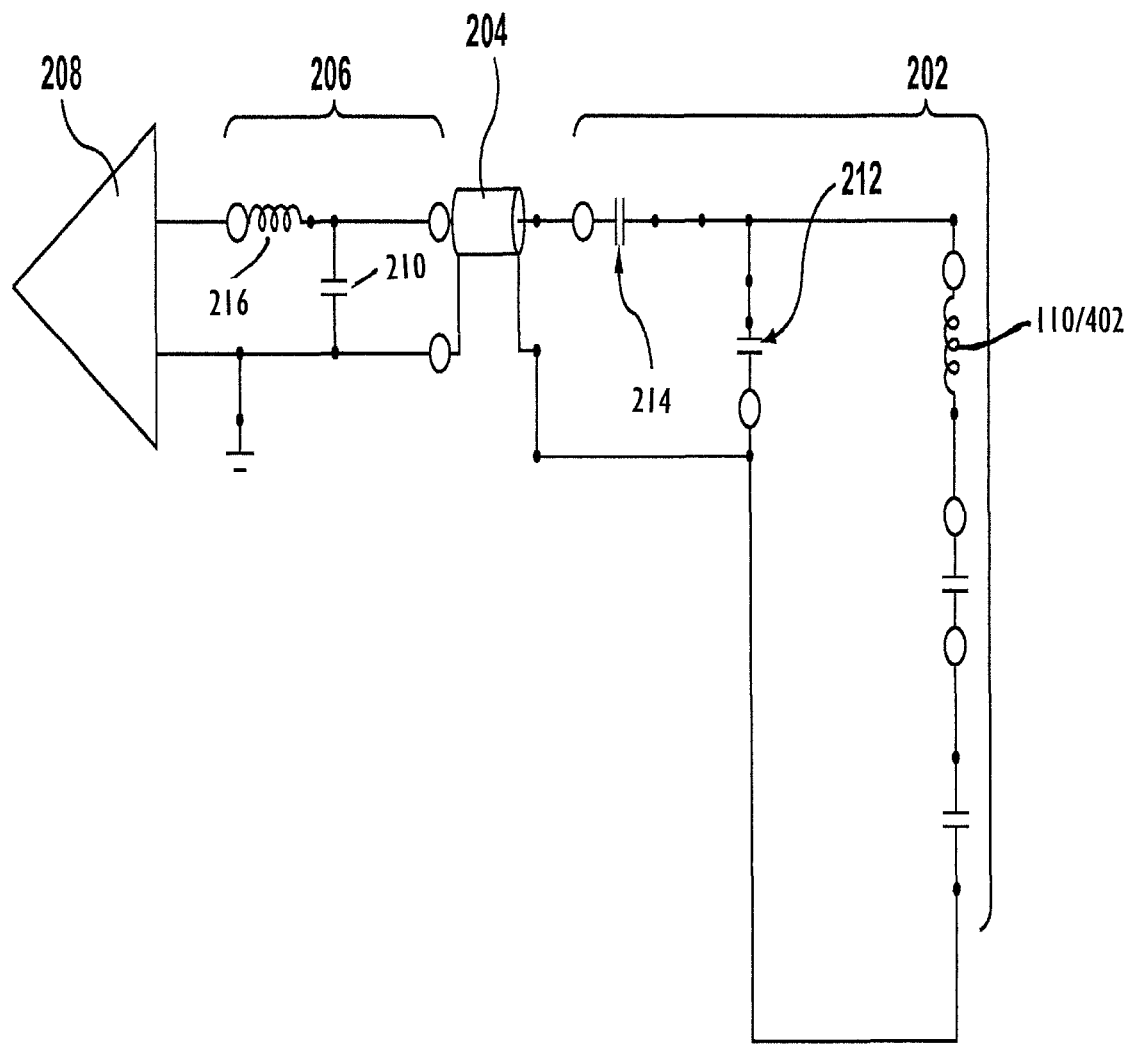
FIG. 2 shows a circuit diagram of an embodiment of an MRI imaging probe.

With reference to FIG. 2, a circuit drawing representative of circuitry associated with each RF coil of the MRI imaging probe is shown, the circuit comprising coil 202, transmission line 204, phase shifter circuit 206 and pre-amp circuit 208. In the embodiment shown, phase shifter circuit 206 consists of inductor 216 and capacitor 210, that operate such that the phase of the electrical input signal is shifted and a desired impedance is input into the pre-amp circuit that resonates with capacitor 212 and capacitor 214 of coil 202. For example, in some embodiments, such as in MRI applications, an impedance of 50 ohms on either side of phase shifter circuit 206 may be desirable.

In the embodiment shown, capacitor 214 will exhibit a high impedance, or Z, value, which can assist in decoupling in coil 202, and which can tend to increase the SNR of the coil and improve the MRI image generated using the MRI imaging probe.

With reference to FIG. 3, an alternative embodiment of a circuit drawing representative of the circuitry associated with each RF coil of the MRI imaging probe of an MRI imaging probe is shown, the circuit comprising coil 302, transmission line 350 and amplifier 330. In the embodiment shown, coil 302 is an MRI receive coil and comprises passive blocking circuit 304, which, in the embodiment shown, is comprised of an inductor and capacitor operating in parallel with cross diodes electrically connected to each. In the embodiment shown, passive blocking circuit 304 operates to reduce current flow which may be induced into coil 302 during the transmit phase of an MRI acquisition, and which can be activated by the body RF transmit field.

Coil 302, in the embodiment shown, further includes active blocking circuit 306, comprising an inductor, capacitor and diode in series. In the embodiment shown, active blocking circuit 306 additionally operates to reduce current flow within coil 302 during the transmit phase of an MRI acquisition using coil 302, to reduce current, and which can be enabled during the transmit phase of the MRI image acquisition.

Coil 302 further comprises coil decoupling circuit 308, which comprises one or more capacitors, some of which may be variable capacitors, electrically connected in parallel. In the embodiment shown, decoupling circuit 308 is comprised of one variable capacitor and one non-variable capacitor, electrically connected in parallel. Coil decoupling circuit 308 operates to decouple currents, such as noise current, and/or other signals that may be induced from other electronic components positioned proximate to coil 302. In some embodiments, such as applications having two coil channels, coil decoupling circuit 308 can decouple coil 302 from another coil channel to reduce any induced current in coil 302 caused by currents, such as noise current, in the other coil channel.

Coil 302 further comprises coil tuning circuit 310 and coil matching circuit 312. Coil tuning circuit 310 operates to tune the resonance frequency of coil 302 and in combination with coil matching circuit 312 gives coil 302 an output impedance of 50 ohms in the embodiment.

Coil 302 is connected to amplifier 330 by transmission line 350, which, in some embodiments, can be a coaxial cable that electrically connects coil 302 to amplifier 330.

In the embodiment shown, amplifier 330 is comprised of coil tuning circuit 332, decoupling and choke circuit 334, phase shifting circuit 336, pre-amp protection circuit 338, pre-amp 340 and output line 342.

Timing circuit 332 is formed by the inductance of the shield with appropriate capacitance. This combination of the embodiment is a tank circuit that will insert a high impedance on the shield to common mode currents that may be induced. Construction of this circuit, as explained above, will tend to provide the appropriate protection to the circuitry of amplifier 330 from the RF induced voltages and currents. In the embodiment, the configuration as shown tends to be advantageous to permit circuit 332 to dissipate sufficient heat during RF transmit pulses.

Decoupling and choke circuit 334 comprises a capacitor and inductor electrically connected in series and operates as an impedance choke to block out high induced currents in amplifier 340.

In the embodiment shown, phase shifter circuit 336 consists of an inductor and two capacitors, connected in shunt across the inductor, pi configuration, that operate such that the phase of the electrical input signal through the phase shifter circuit 336 is shifted, while maintaining an input and output impedance of 50 ohms. In other embodiments, a T configuration may be used. In either case, the circuit is to adjust the phase lag introduced by the transmission line 350 and circuit 332, to a phase equal to a phase necessary to resonant with matching circuit 312 and circuit 310 of coil 302.

Pre-amp protection circuit 338, as shown in the embodiment, forms a voltage limiter that operates to prevent voltage spikes into pre-amp circuit 340.

In the embodiment shown, amplifier 340 amplifies the received signal and outputs the amplified signal through output line 342, which can be connected to an MR receiver. This signal can then be amplified and converted to digital form so MRI imaging software can interpret the amplified signals output through output line 342, and use such signals to generate an MRI image of the tissue being imaged.

The present invention has been described with regard to specific embodiments. The scope of the claims should not be limited by the preferred embodiments set forth in the examples, but should be given the broadest interpretation consistent with the description as a whole. It will be obvious to persons skilled in the art that a number of variants and modifications can be made without departing from the scope of the invention as described herein.

The invention claimed is:

1. An endocavity MRI imaging probe for use in a magnetic resonance imager (MRI) which generates a main magnetic field, the probe comprising:
 a coil section having an imaging coil, the coil section being configured for insertion into an orifice of a patient;

a handle section connected to the coil section, the handle section being configured to be grasped manually by a clinician during positioning of the handle section having:
- a phase shifter circuit comprising a set of inductors and capacitors electrically connected, a coaxial cable winding including a coaxial cable electrically connected to the imaging coil and wound around a cylinder; and
- a pre-amp circuit mounted on a substrate and electrically connected to the coaxial cable winding, wherein at least a portion of the substrate passes through and is supported by the coaxial cable winding.

2. The probe of claim 1, wherein the imaging coil includes a passive tuning circuit.

3. The probe of claim 2, further comprising a fiducial marker disposed in the coil section.

4. The probe of claim 3, wherein the coil section and the handle section are cylindrical and further including:
a cylindrical neck section connecting the coil section to the handle section, the neck section having a smaller diameter than that of the coil and handle sections, the neck section, the coil section, the handle section and the neck section being aligned along a longitudinal axis.

5. The probe of claim 4, wherein the substrate is planar and is parallel to the longitudinal axis.

6. The probe of claim 1, comprising:
- a second imaging coil in the coil section, the second imaging coil having a second passive tuning circuit and electrically connected to the first imaging coil through a decoupling circuit;
- a second set of inductors and capacitors electrically connected, a second coaxial cable winding electrically connected to the second imaging coil and wound cylindrically around the slot of the first cylindrical winding; and
- a second pre-amp circuit mounted on the substrate electrically connected to the second cylindrical winding.

7. The probe of claim 6, wherein the first and second coaxial cylindrical windings, the coaxial cables of the first and second coaxial cylindrical windings being wound on the cylinder radially relative to each other.

8. The probe of claim 6, wherein the first and second coaxial cylindrical windings, the coaxial cables of the first and second coaxial cylindrical windings being wound side-by-side on the cylinder.

9. The probe of claim 8, wherein the second coaxial cable windings are wound in opposite directions around the cylinder.

10. The probe of claim 4, further comprising a coil shell surrounding the coil section and the neck section.

11. The probe of claim 10, wherein the coil section further has a passage therethrough, and the coil shell defines a slot therethrough aligned with the passage, the slot and passage permitting passage of a medical instrument to pass through the coil section of the probe.

12. The probe of claim 11, wherein the slot extends from a first surface region of the coil shell at the neck section, to a second surface region of the coil shell at the coil section.

13. The probe of claim 10, further comprising a handle shell surrounding the handle section, the handle shell being connected to the coil shell.

14. An endorectal MR imaging probe for use in imaging a prostate of a patient disposed in a magnetic resonance imager, the probe comprising:
a coil section including:
first and second RF coils,
a decoupling circuit configured to decouple the first and second RF coils,
blocking circuitry configured to block currents in the first and second RF coils during a transmit phase of an MRI acquisition, and
tuning and matching circuitry configured to tune a resonance frequency and an output impedance of the first and second RF coils;
a neck section connected with the coil section and including a coaxial transmission lines connected with the tuning and matching circuitry;
a handle section connected with the neck section, the coil section, the neck section and the handle section being axially aligned, the handle section including:
tuning circuitry connected with the coaxial transmission lines,
phase shift circuitry connected with the tuning circuitry, and
preamplifier circuits connected with the phase shift circuitry.

15. The probe of claim 14, wherein the phase shift circuitry includes:
first and second coaxial cable sections, each connected via the tuning circuitry with one of the transmission lines, the first and second coaxial cables being wound around a cylinder; and
wherein the preamplifier circuits are mounted on a substrate, the substrate being supported by the cylinder of the phase shift circuitry.

16. The probe of claim 15, wherein the first and second coaxial cables are wound around the cylinder in opposite directions.

17. An endocavity magnetic resonance imaging probe comprising:
a coil section including at least one imaging coil, the coil section being configured for insertion into an orifice of a patient, the imaging coil being configured to receive RF resonance signals induced by a magnetic resonance imager which is configured to receive at least a portion of the patient adjacent the orifice;
a neck section connected with the coil section, the neck section including a transmission line configured to convey the resonance signals received by the imaging coil;
a handle section connected with the neck section, the handle section being configured to be grasped by a clinician during positioning of the coil section in the orifice, the handle section including:
a phase shift circuit including a coaxial cable wound around a cylinder, the coaxial cable which is wound around the cylinder is electrically connected with the transmission lines to phase shift the received resonance signal, and
a preamplifier circuit mounted on a substrate, the substrate passing through and being supported by the phase shift circuit cylinder, the preamplifier circuit being connected with the phase shift circuit and configured to amplify the phase shifted received resonance signal.

18. The probe of claim 17, wherein the coil section, the neck section, and the handle section are aligned along a longitudinal axis and the neck section being smaller in cross-section than the coil section and wherein the cylinder of the phase shift circuit and the substrate are aligned along the longitudinal axis.

19. The probe of claim 18, wherein the neck and coil portion define a passage therethrough, the passage being configured to receive a medical instrument inserted in through the neck section and exiting through the coil section.

20. The probe of claim 19, wherein:
the coil section further includes a second RF coil and a decoupling circuit for decoupling the first and second RF coils;
the neck section includes a pair of transmission lines; and
the phase shift circuit disposed in the handle section includes first and second coaxial cables which are wound in opposite directions around the cylinder.

* * * * *